(12) United States Patent
Kanade et al.

(10) Patent No.: US 9,746,401 B2
(45) Date of Patent: Aug. 29, 2017

(54) MULTI-AXIS UNIVERSAL MATERIAL TESTING SYSTEM

(71) Applicants: Udayan Kanade, Pune (IN); Manohar Joshi, Pune (IN); Sanat Ganu, Pune (IN)

(72) Inventors: Udayan Kanade, Pune (IN); Manohar Joshi, Pune (IN); Sanat Ganu, Pune (IN)

(*) Notice: Subject to any disclaimer, the term of this patent is extended or adjusted under 35 U.S.C. 154(b) by 62 days.

(21) Appl. No.: 14/763,862

(22) PCT Filed: Mar. 28, 2014

(86) PCT No.: PCT/IB2014/060284
§ 371 (c)(1),
(2) Date: Jul. 28, 2015

(87) PCT Pub. No.: WO2014/115130
PCT Pub. Date: Jul. 31, 2014

(65) Prior Publication Data
US 2015/0377754 A1    Dec. 31, 2015

(30) Foreign Application Priority Data

Jan. 28, 2013 (IN) .......................... 240/MUM/2013
Jun. 13, 2013 (IN) ......................... 2011/MUM/2013

(51) Int. Cl.
*G01N 3/04* (2006.01)
*G01N 3/02* (2006.01)
(Continued)

(52) U.S. Cl.
CPC ............... *G01N 3/02* (2013.01); *G01N 3/068* (2013.01); *G01N 3/08* (2013.01);
(Continued)

(58) Field of Classification Search
CPC  G01N 3/04; G01N 3/08; G01N 3/068; G01N 3/10; G01N 2203/0016;
(Continued)

(56) References Cited

U.S. PATENT DOCUMENTS

| 4,073,185 A * | 2/1978 | Griffin ..................... G01N 3/04 73/833 |
| 7,509,882 B2 * | 3/2009 | Monteiro ................. G01N 3/08 73/862.046 |
| 7,533,557 B1 * | 5/2009 | Mott ....................... G01N 3/303 73/12.14 |

FOREIGN PATENT DOCUMENTS

| JP | 2000162104 A | 6/2000 |
| WO | WO2005040765 A2 | 5/2005 |

* cited by examiner

*Primary Examiner* — Blake A Tankersley

(57) ABSTRACT

A universal materials testing machine is disclosed. In one embodiment, the machine comprises a plurality of grips holding a circular material specimen sheet; the grips being capable of pulling the material specimen radially outward. Each grip is connected to a force measurement sensor such as a load cell. The grip and the load cell assembly is connected to a linear actuator assembly. The linear actuator assembly comprises a motor connected to an arm that can move along a straight line. The actuator pulls or pushes the load cell and grip assembly. A camera module captures images of the specimen while being stretched or released. A data processing system gathers camera module images along with force measurements from the load cells. An analysis module running on the data processing unit computes stress and strain measurements and fits them to user selectable material model.

4 Claims, 14 Drawing Sheets

(51) Int. Cl.
*G01N 3/06* (2006.01)
*G01N 3/08* (2006.01)
(52) U.S. Cl.
CPC ............... *G01N 2203/0254* (2013.01); *G01N 2203/0282* (2013.01); *G01N 2203/0641* (2013.01); *G01N 2203/0647* (2013.01)
(58) Field of Classification Search
CPC ... G01N 2203/0017; G01N 2203/0254; G01N 2203/0278; G01N 2203/0282; G01N 2203/0641; G01N 2203/0647; G01N 2203/0447
See application file for complete search history.

MULTI-AXIS UNIVERSAL MATERIAL TESTING SYSTEM

This application claims priority from provisional patent application 2011/MUM/2013 titled "Multi-Axis Universal Material Testing System" filed in Mumbai, India on 13 Jun. 2013.

TECHNICAL FIELD

The present invention relates to a material testing system. Particularly, the invention relates to a multiple axes universal materials testing system.

BACKGROUND ART

Material properties can be characterized by testing systems. Depending on the material and type of analysis, testing systems may have different mechanisms of characterizing material properties. Material testing systems known in the art are used to characterize materials such as metals, polymers, rubbers, textiles, bio-materials, adhesives, composites etc. Typically, materials are subjected to forces in various configurations and their responses are analyzed.

SUMMARY

A universal materials testing machine is disclosed. In one embodiment, the machine comprises a plurality of grips holding a circular material specimen sheet; the grips being capable of pulling the material specimen radially outward. Each grip is connected to a force measurement sensor such as a load cell. The grip and the load cell assembly is connected to a linear actuator assembly. The linear actuator assembly comprises a motor connected to an arm that can move along a straight line. The actuator pulls or pushes the load cell and grip assembly. A camera module captures images of the specimen while being stretched or released. A data processing system gathers camera module images along with force measurements from the load cells. An analysis module running on the data processing unit computes stress and strain measurements and fits them to user selectable material model.

The above and other preferred features, including various details of implementation and combination of elements are more particularly described with reference to the accompanying drawings and pointed out in the claims. It will be understood that the particular methods and systems described herein are shown by way of illustration only and not as limitations. As will be understood by those skilled in the art, the principles and features described herein may be employed in various and numerous embodiments without departing from the scope of the invention.

BRIEF DESCRIPTION OF THE DRAWINGS

The accompanying drawings, which are included as part of the present specification, illustrate the presently preferred embodiment and together with the general description given above and the detailed description of the preferred embodiment given below serve to explain and teach the principles of the present invention.

DETAILED DESCRIPTION

A universal materials testing machine is disclosed. In one embodiment, the machine comprises a plurality of grips holding a circular material specimen sheet; the grips being capable of pulling the material specimen radially outward. Each grip is connected to a force measurement sensor such as a load cell. The grip and the load cell assembly is connected to a linear actuator assembly. The linear actuator assembly comprises a motor connected to an arm that can move along a straight line. The actuator pulls or pushes the load cell and grip assembly. A camera module captures images of the specimen while being stretched or released. A data processing system gathers camera module images along with force measurements from the load cells. An analysis module running on the data processing unit computes stress and strain measurements and fits them to user selectable material model.

Figure 1:
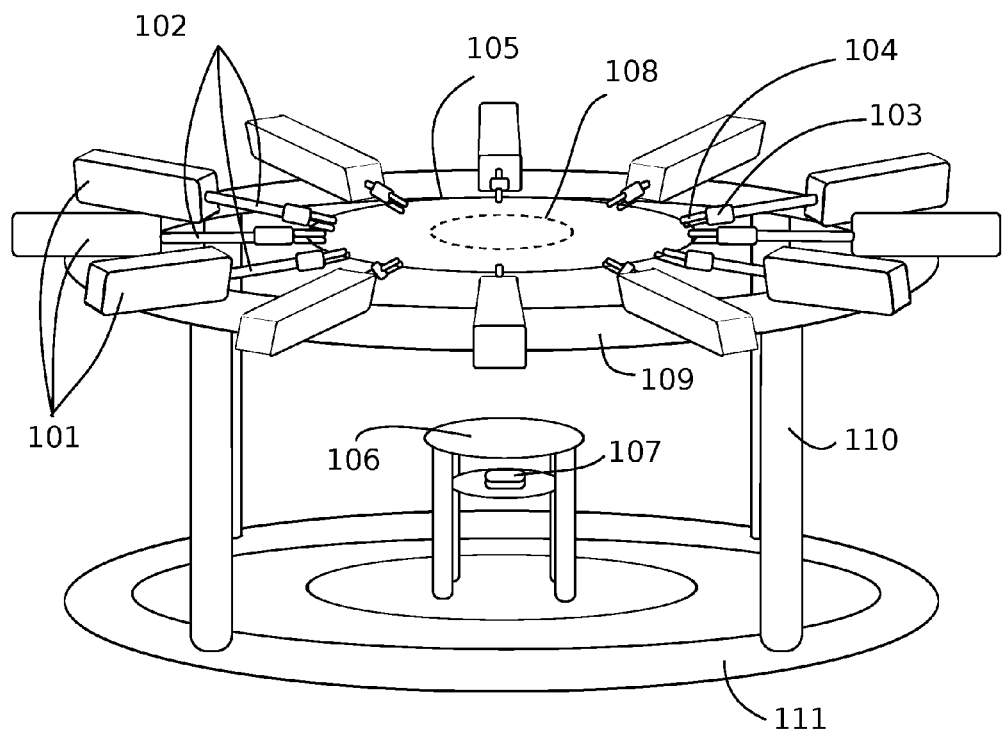
FIG. 1 illustrates a block diagram of a materials testing machine, according to one embodiment of the present invention.

FIG. 1 illustrates a block diagram of a materials testing machine 199, according to one embodiment of the present invention. The system comprises a plurality of linear actuators 101 arranged in a circle with actuator arms 102 pointing to the center of the circle on which the actuators are arranged. Actuators are mounted in a plane using a reference plate 109. The plate 109 is mounted on a base plate 111 using leg supports 110. Each linear actuator has an independently controllable motor that can be controlled to push the actuator arm towards the center of the said circle or away from it. Each linear actuator arm is connected to a force measurement sensor such as a load cell depicted by 103. A gripping mechanism such as a wedge grip or a roller grip is connected to the force measurement sensor. 104 depicts a gripping mechanism. Test specimen 105 is in the form of a circular sheet of certain thickness. 105 depicts test specimen in a stretched state held along its circumference by grips such as 104. 108 depicts the test specimen boundary when it is not stretched or compressed by the plurality of grips. This stretch approximates a uniform stretch along all directions in a plane—known as "biaxial" stretch. The test specimen may be primarily circular in nature, with extentions jutting out in exactly such directions that the grippers may grip these extensions.

107 is a camera module which captures images of the specimen while it is stretched or compressed. 106 is a transparent cover that protects the camera module. The camera may capture images of the specimen and the apparatus either from above the specimen or from below the specimen. A data collection and processing system gathers data from the force measurement sensors and the camera module. Force measurement data is collected from all force measurement sensors at various stretched or compressed states of the test specimen. In a particular analysis performed on the force measurements, specimen stress is calculated. Images captured by the camera module are analyzed for characterizing how the specimen gets stretched. In a particular analysis, the specimen strain is calculated from the image data. The data processing system fits this data to various material models that may be of interest.

In an embodiment of the present invention, the specimen is marked with patterns such as concentric circles, or a well defined pattern of spots, such as circular, elliptical or triangular spots. The camera module is used to track the motion of the marked patterns and calculate displacements at various locations on the specimen using machine vision techniques.

In an embodiment of the present invention, the camera module is used to track the motion of actuator arms and measure the displacement of each actuator arm from its initial position using machine vision techniques.

In an embodiment of the present invention, the actuator arms have a built-in displacement sensor to measure displacement from a present initial position.

In an embodiment of the present invention, the actuator arms have built-in displacement sensors to measure displacement from a preset initial position and displacement of specimen being stretched is predicted using a mathematical model of the specimen.

In an embodiment of the present invention, the camera module is used to detect failure modes such as a non-functional linear actuator or specimen slipping out of a grip etc. using machine vision techniques.

In an embodiment of the present invention only two actuators are used to stretch a rectangular specimen to perform uniaxial stretching or compression.

In an embodiment of the present invention, only two actuators are used with grip attachments that grip along the entire specimen edge. Stretching with such grips enables shear stretching.

In an embodiment, a single apparatus can perform two or all three of uniaxial, biaxial and shear stretching. For uniaxial, only two actuators are engaged. For biaxial all actuators are engaged. For shear, two actuators are engaged, with a special attachment or modification for shear, or by gripping the specimen very closely to the opposite grip.

In an embodiment of the present invention, the actuators increase and decrease the stretch of the specimen at a desired frequency.

In an embodiment of the present invention, the speed at which the specimen is stretched or the stretch is reduced can be set as a function of the amount of stretch.

In an embodiment of the present invention, a reference annular plate such as depicted by 109 is precision machined to be in a plane and actuators such as 101 are assembled on it.

In an embodiment of the present invention, a reference annular plate such as depicted by 109 is precision machined to be in a plane and actuators such as 101 are assembled on a separate structure. Shims are used to adjust the level of the actuators on the structure such that all actuators are the same level as the the reference plate 109 ensuring that they lie in the same plane.

In an embodiment of the present invention, the frame housing the linear actuators is a rectangular or other shaped frame constructed using truss structures.

Figure 2:
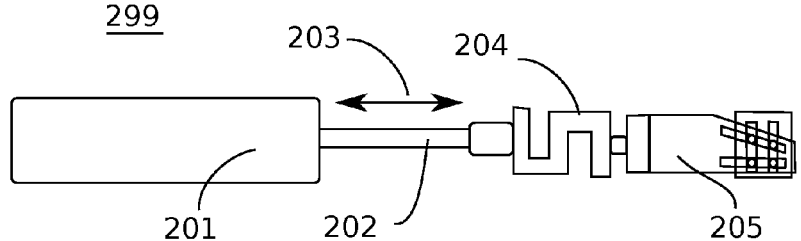
FIG. 2 illustrates an exemplary linear actuator arm according to one embodiment of the present invention.

FIG. 2 illustrates an exemplary linear actuator arm 299 according to one embodiment of the present invention.

Linear actuator arm 299 comprises motor housing 201, retractable arm 202 that can move forward or backward along a straight line depicted by 203. 204 is a force measurement sensor such as a load cell. 204 is mechanically coupled to 203 by a coupling element. 205 is a grip mechanism such as a wedge grip. 205 is mechanically coupled to 204 by a coupling element. The linear actuator arm moves forward or backward using a rack-and-pinion arrangement, a screw or ball-screw arrangement, or using hydraulic, pneumatic or electromagnetic linear actuators.

Figure 3:
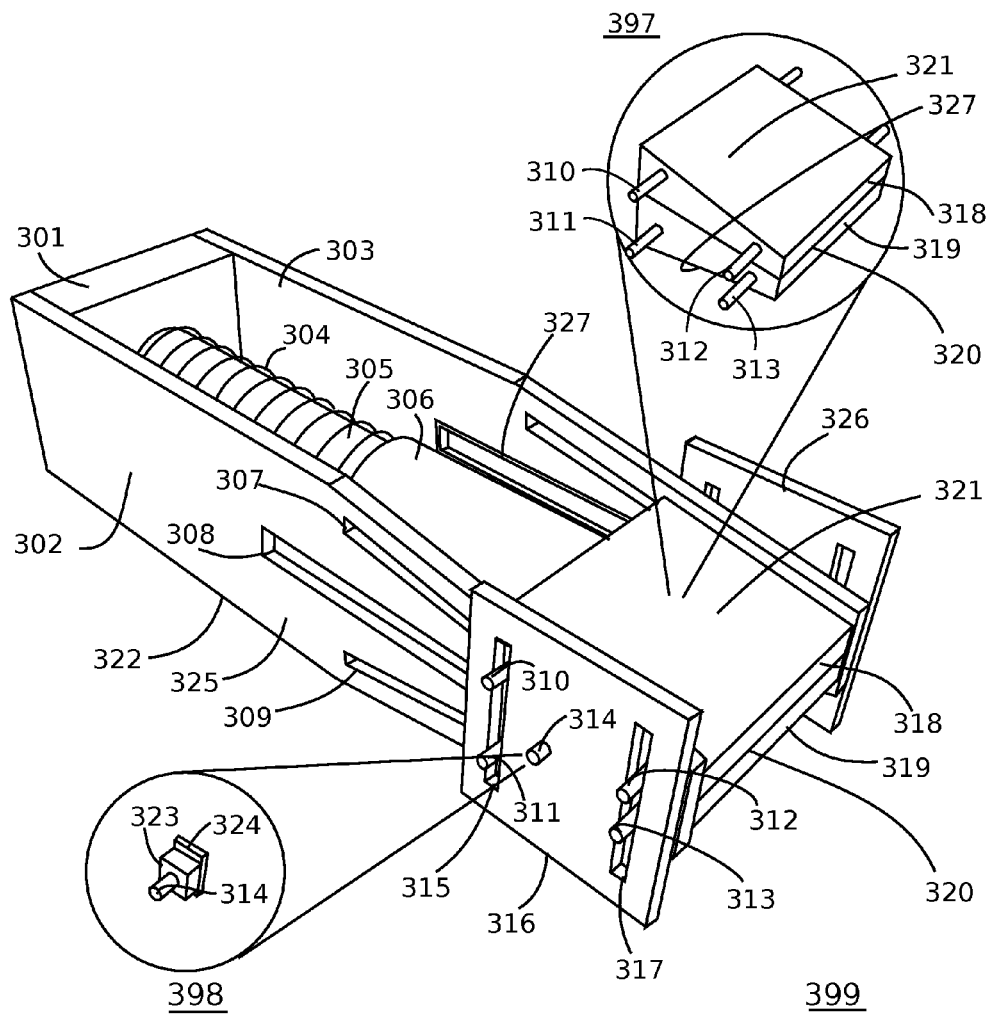
FIG. 3 illustrates a block diagram of an exemplary gripping mechanism according to one embodiment of the present invention.

FIG. 3 illustrates a block diagram of an exemplary gripping mechanism 399 according to one embodiment of the present invention.

The gripping mechanism comprises a base rectangular block 301 which has a cylindrical extension 305. A spring 304 is mounted on the cylindrical extension 305. The cylindrical extension 305 may be solid or a hollow cylinder of a particular inner and outer diameter. A hollow cylinder 306 is concentric with cylindrical extension 305. The inner diameter of 306 is greater than the outer diameter of 305. The hollow cylinder 306 slides over cylindrical extension 305 and compresses the spring 304 as it slides towards the base block 301.

Plates 302 and 303 are mechanically mounted on the two sides of base block 301. Plates 302 and 303 are identical or reflection symmetric to each other. 307 and 309 are rectangular slits cut out from the plate 302. Edges of slits 307 and 309 make certain angles with the horizontal edge 322 of the plate 302, in such a way that the slits are nearer to each other towards the front, and away from each other towards the back. The angles may be equal and opposite, or the angles may be different. In an embodiment, the lower slit 309 is horizontal, whereas the upper slit 307 is slanted. 308 represents a rectangular cavity cut out from the plate 302 with a rectangular groove structure that holds the plate 316 using a key whose cylindrical end is depicted by 314. 398 is an unoccluded view of the key that holds plate 316 together with plate 302. The inner face of plate 316 rests on the block 323 of the key depicted in 398. The block 323 of the key shown in 398 extends above (in front of) the surface of plate 302 and prevents the inner surface of plate 316 from contacting the outer surface 325 of plate 302. Block 324 of the key shown in 398 rests on a groove structure in the slit 308 and prevents the key from falling out of the slit 308. The plate 326 is identical to plate 316, or it is reflection symmetric to plate 3'6. The plates 316 and 326 together with their keys are free to move along the identical horizontal slits 308 and 327 respectively. The plates 316 and 326 may be rectangular in shape.

318 and 319 depict wedge shaped solid blocks with cylindrical pins 310, 311, 312 and 313 extending from one side. Symmetrically, pins are also extending from the other side. 397 depicts an unoccluded view of the wedge blocks 318 and 319. The faces of the wedge blocks along edge 320 are parallel to each other and the edge 322 of the plate 302. These faces form the specimen holding area or gripper. The faces opposite to these faces such as face 321 and face 327 are at a certain angle to the horizontal. This angle may be the same as the angle between the long edge of slit 307 and the horizontal edge 322 of the plate 302. Pins 310 and 311 fit into the vertical slit 315 of plate 316 as well as the slanted slits 307 and 309 of plate 302. Similarly, Pins 312 and 313 fit into the vertical slit 317 of plate 316 and the slanted slits 307 and 309 of plate 302. A similar arrangement of pins and slits exists on the other side with plates 326 and 303. This arrangement of pins and slits constrains the motion of the wedge blocks in a particular way. Whenever plates 316 and 326 are pulled towards the base block 301, the wedge blocks travel along the slit edges and open up along the edge 320. At the same time, the wedge blocks push the cylindrical component 306 towards the base block 301 causing the spring to compress. Specimen can be loaded when the wedge blocks open up. Upon releasing the plates 316 and 326, the spring 304 pushes the cylindrical component 306 which pushes the wedge blocks away from base block 301 and the wedge faces move to close the gap between faces along edge 320. This causes the specimen to be gripped with a certain force. After loading the specimen in this manner, whenever the specimen is pulled away from base block 301, the faces slide away from the base block 301 and further close the gap between the wedge faces along edge 320 and hence grip the specimen with a greater force. The specimen can be released from the gripping faces by pulling plates 316 and 326 towards base block 301.

In an embodiment of the present invention, the wedge shaped block faces that hold the specimen have serrations for increasing friction. Alternatively surface treatment or coating conducive to better gripping of the specimen may be used.

In an embodiment of the present invention, extension springs are used to pull on the wedge blocks to close the gap between them. For example, instead of the spring 304 and cylinders 305 and 306, a spring may be attached between the peg 314 and a point on the plate 302 towards the front of the plate 302 (opposite to the end where base block 301 is attached). The spring will extend as the wedge blocks are pushed further back, creating force that will cause the wedge blocks to move forward, and hence grip closer/tighter.

In an embodiment of the present invention, a vertical rod slides in a cylindrical cavity that extends in both the wedge blocks for coupling their horizontal motion. In this embodiment, plates 316 and 326 may not be required. Matching vertical cylindrical cavities are formed in the gripping faces of the wedge blocks. A vertical rod is placed in such a way that in all positions of the gripper, part of the vertical rod will be in the cavity in the lower wedge block and part of the vertical rod will be in the cavity in the upper wedge block.

In an embodiment of the present invention, the wedge shaped blocks and the grip housing are marked with distinct patterns. A camera module such as the one described in the system of FIG. 1 is used to track the relative motion between the wedge blocks and the grip housing by tracking the distinctly marked patterns using machine vision.

In an embodiment of the present invention the plates 316 and 326 have handles to allow an operator to slide them back towards the base block 301 for the purpose of loading a specimen manually.

In an embodiment of the present invention, the wedge grip plates 316 and 326 have a visible calibrated distance scale along the horizontal axis indicating the gap between the gripping faces of the wedge blocks at various positions of the said plates.

In general, a gripping mechanism of the present invention comprises the following means. It comprises means for gripping, the means usually being two blocks, the specimen being gripped between one face of each block, the said faces always remaining parallel to each other. The gripping mechanism further comprises means for the gripping blocks to slide forward and back in such a way that the further back the mechanism slides, the more is the gap created between the gripping faces of the gripping blocks. In it's most forward position, the gap is zero, or some minimum gap. Furthermore, there may also be present means that pull or push the gripping blocks forward, such as springs that pull or push the gripping blocks to it's forward-most (i.e. most tightly gripped) position. The gripping mechanism further comprises means to ensure that the two gripping blocks always move parallel to each other and to the whole structure, and the gripping blocks move forward and behind in tandem with each other, i.e. by the same amount. When the two gripping blocks move back and hence away from each other, the top gripping block moves further up. The bottom gripping block moves further down, or remains in place.

Figure 4:
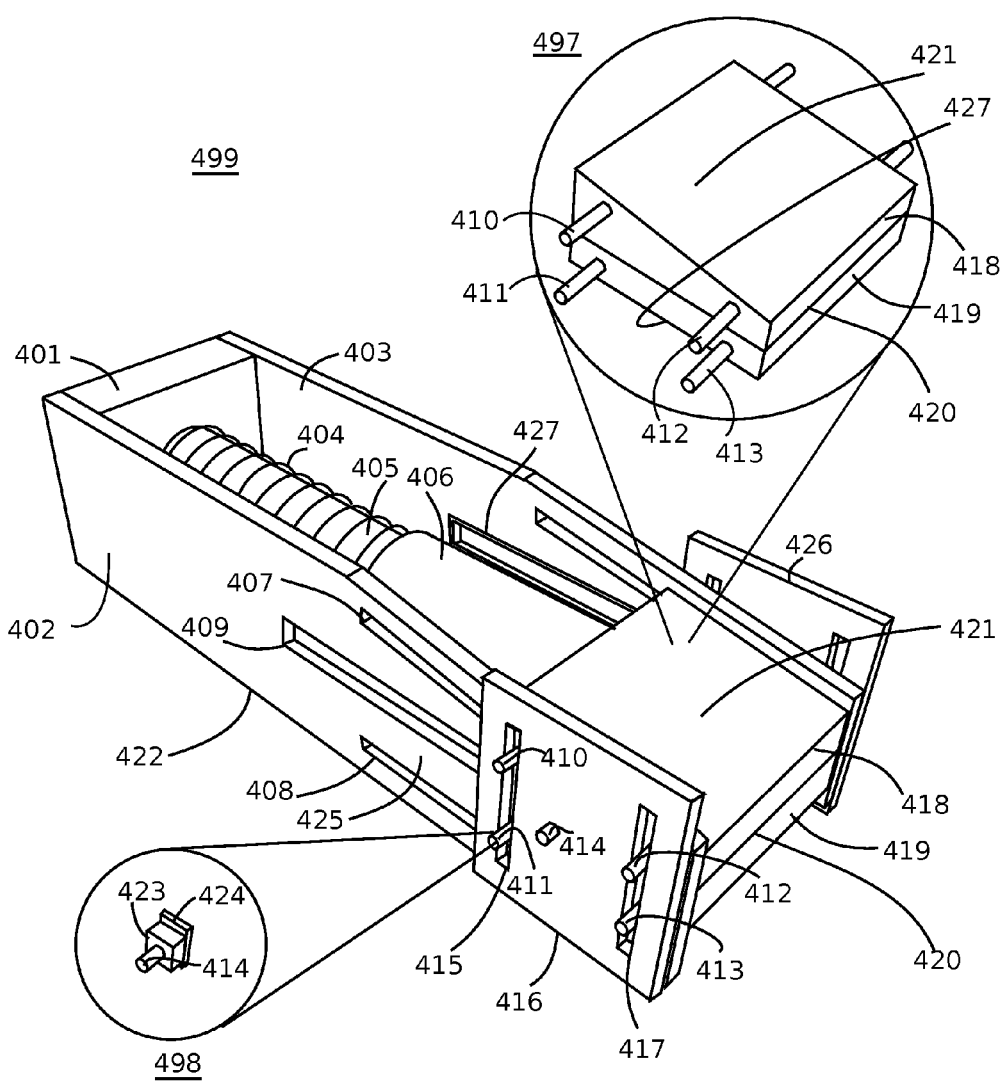
FIG. 4 illustrates a block diagram of an exemplary gripping mechanism according to an embodiment of the present invention.

FIG. 4 illustrates a block diagram of an exemplary gripping mechanism 499 according to an embodiment of the present invention.

The gripping mechanism comprises a base rectangular block 401 which has a cylindrical extension 405. A spring 404 is mounted on the cylindrical extension 405. The cylindrical extension 405 may be solid or a hollow cylinder of a particular inner and outer diameter. A hollow cylinder 406 is concentric with cylindrical extension 405. The inner diameter of 406 is greater than the outer diameter of 305. The hollow cylinder 406 slides over cylindrical extension 405 and compresses the spring 404 as it slides towards the base block 401.

Plates 402 and 403 are mechanically mounted on the two sides of base block 401. Plates 402 and 403 are identical or reflection symmetric to each other.

407 and 408 are rectangular slits cut out from the plate 402. The long edge of slit 407 makes a certain angle with the horizontal edge 422 of the plate 402. The long edge of slit 408 is parallel with the horizontal edge 422 of the plate 402. Slit 409 is a rectangular cavity cut out from the plate 402 with a rectangular groove structure that holds the plate 416 using a key whose cylindrical end is depicted by 414. 498 depicts an unoccluded view of the key that holds plate 416 together with plate 402. The inner face of plate 416 rests on the block 423 of the key depicted in 498. The block 423 of the key shown in 498 extends above the surface of plate 402 and prevents the inner surface of plate 416 from contacting the outer surface 425 of plate 402. Block 424 of the key shown in 498 rests on a groove structure in the slit 409 and prevents the key from falling out of the slit 409. The rectangular plate 426 is identical to plate 416, or reflection symmetric to it. The rectangular plates 416 and 426 together with their keys are free to move along the identical horizontal slits 409 and 427 respectively.

418 and 419 depict distinct wedge shaped solid blocks with cylindrical pins 410, 411, 412 and 413 extending from one side. Symmetrically, cylindrical pins also extend from the other side. 497 depicts an unoccluded view of the wedge blocks 418 and 419. The faces of the wedge blocks along edge 420 are parallel to each other and the edge 422 of the plate 402. These faces form the specimen holding area or gripper. Face 421 of the wedge block 418 is at a certain angle to the horizontal plane containing the edge 422 of plate 402. This angle may be the same as the angle between the long edge of slit 407 and the horizontal edge 422 of the plate 402. Face 427 of the wedge block 419 is parallel to its face along the edge 420. Pins 410 and 411 fit into the vertical slit 415 of plate 416 as well as the slanted slits 407 and 408 of plate 402. Similarly, Pins 412 and 413 fit into the vertical slit 417 of plate 416 and the slanted slits 407 and 408 of plate 402. A similar arrangement of pins and slits exists on the other side of the grip which has plates 426 and 403. This arrangement of pins and slits constrains the motion of the wedge blocks in a particular way. Whenever plates 416 and 426 are pulled towards the base block 401, the wedge blocks travel along the slit edges and open up along the edge 420. As they move, the wedge blocks push the cylindrical component 406 towards the base block 401 causing the spring to compress. A specimen can be loaded when the wedge blocks open up. Upon releasing the plates 416 and 426, the spring 404 pushes the cylindrical component 406 which pushes the wedge blocks away from base block 401 and the wedge faces move so as to close the gap between faces along edge 420. This causes the specimen to be gripped with a certain force. After loading the specimen in this manner, whenever the specimen is pulled away from the base block 401, upon exerting a certain pull force, the faces slide away from the base block 401 and further close the gap between the wedge faces along edge 420 and hence grip the specimen with a greater force. The specimen can be released from the gripping faces by pulling plates 416 and 426 towards base block 401.

In an embodiment of the present invention, the wedge shaped block faces have serrations for increasing friction.

In an embodiment of the present invention, extension springs are used to pull on the wedge blocks to close the gap between them.

In an embodiment of the present invention, a vertical rod slides in a cylindrical cavity that extends in both the wedge blocks for coupling their horizontal motion.

Figure 5:
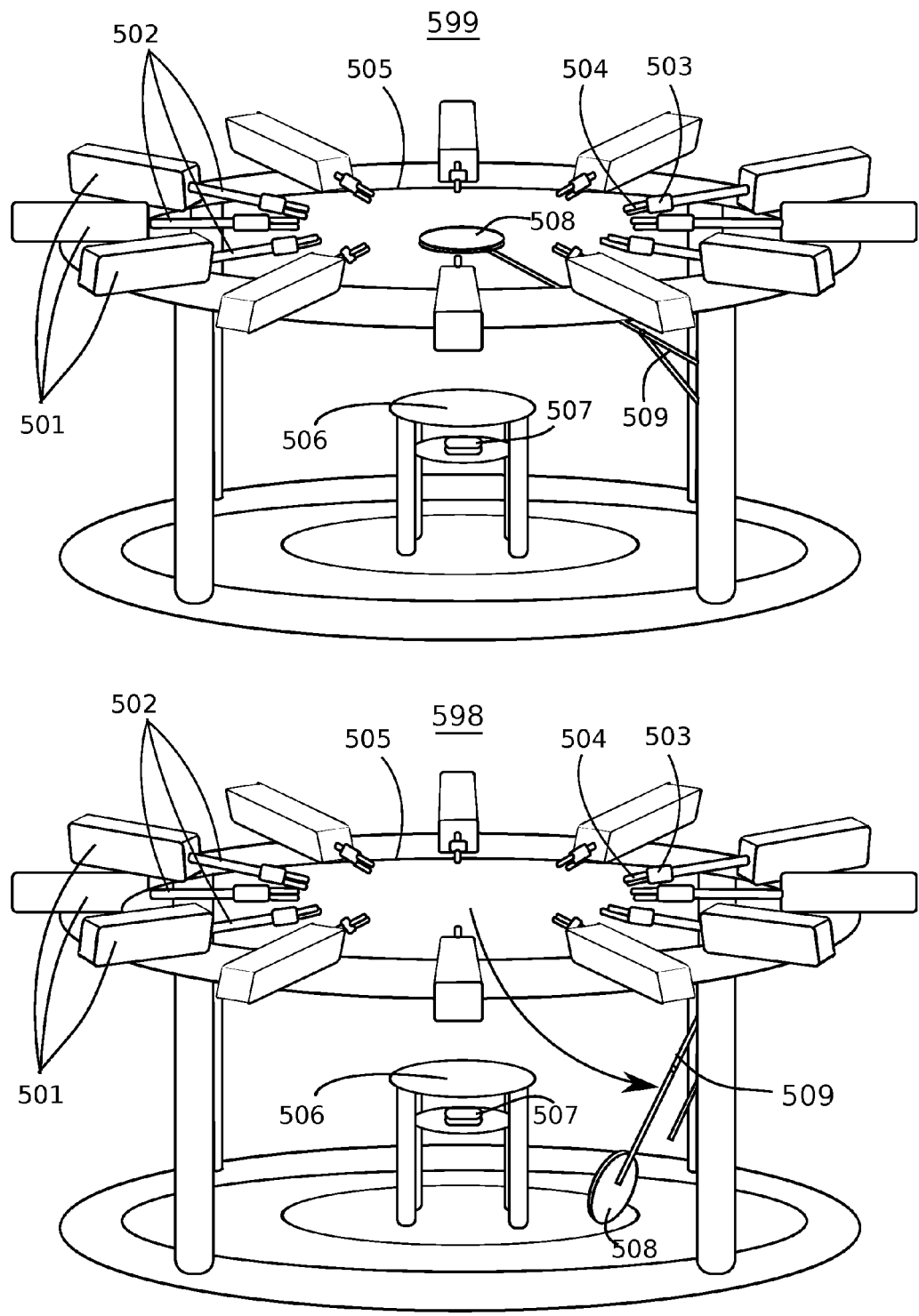
FIG. 5 illustrates block diagrams of a materials testing machine in two configurations, explaining working of a retractable specimen loading mechanism, according to an embodiment of the present invention.

FIG. 5 illustrates block diagrams of a materials testing machine in two configurations 599 and 598 explaining working of a retractable specimen loading mechanism, according to an embodiment of the present invention.

The system comprises a plurality of linear actuators 501 arranged in a circle with actuator arms 502 pointing to the center of the circle on which the actuators are arranged. Each linear actuator has an independently controllable motor that can be controlled to push the actuator arm towards the center of the said circle or away from it. Each linear actuator arm is connected to a force measurement sensor such as a load cell depicted by 503. A gripping mechanism such as a wedge grip or a roller grip is connected to the force measurement sensor. 504 depicts a gripping mechanism. 507 is a camera module which captures images of the specimen while it is stretched or compressed. 506 is a transparent cover that protects the camera module. 508 is a specimen holder plate with support 509. 599 is a configuration of the machine where the specimen holder plate is extended such that it is level with the grip surfaces. 598 is a configuration of the machine where the plate is retracted such that the specimen holder plate is away from the view of the camera module 507.

In an embodiment, the specimen holder plate 508 has particular boundary to accommodate various specimen shapes. In another embodiment, the specimen holder plate has particular boundary to allow the specimen holding grips to enter into the specimen holding area for easy specimen loading.

In an embodiment, the specimen holding plate 508 is supported by more than one supporting member.

Figure 6A:
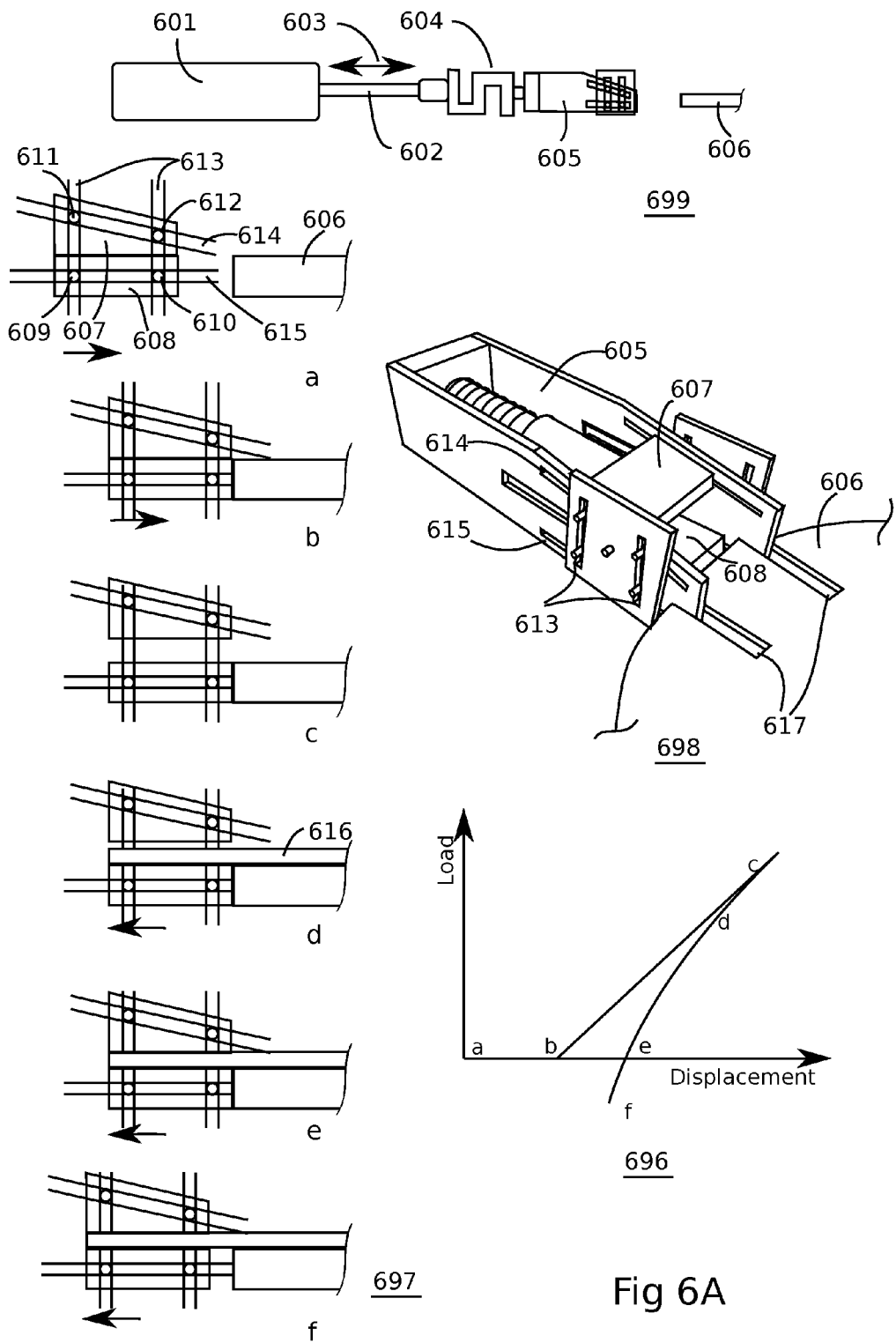
FIG. 6A illustrates steps in an exemplary method to load the specimen into a grip according to an embodiment of the present invention.

FIG. 6A illustrates steps in an exemplary method to load the specimen into a grip according to an embodiment of the present invention.

699 depicts a linear actuator arm comprising motor housing 601, retractable arm 602 that can move forward or backward along a straight line depicted by 603. 604 is a force measurement sensor such as a load cell. 604 is mechanically coupled to 602 by a coupler. 605 is a grip mechanism such as a wedge grip. 605 is mechanically coupled to 604 by a coupler. 606 is a specimen holding plate which can be used to place a specimen to be loaded into the grip assembly 605. The specimen loading plate boundary is such that the vertical grip faces can enter into the specimen holding area as shown in 698 through slits 617. The width of the slits 617 may be much larger than the entering plate thickness. For example, such a slit may be so large as to accommodate a right plate of a grip mechanism and a left plate of an adjoining grip mechanism.

697 depicts sequence of steps that occur in an exemplary method to load the specimen into the grip 605 where 605 is a wedge grip such as the one depicted in 698. 607 and 608 depict two wedge blocks in wedge grip 605 of 698. As shown in 697, the motion of the wedge block 607 is constrained by slits in external plates such that the wedge block pins 611 and 612 stay within the slanted slit boundary 614 and vertical slit boundary 613. Similarly, the motion of the wedge block 608 is constrained by external plates such that the wedge block pins 609 and 610 stay within the horizontal slit boundary 615 and vertical slit boundary 613. 606 depicts the specimen holding plate on which the specimen can be placed for loading into the grip.

Frames (a) to (f) in 697 depict the steps in specimen loading. 696 depicts the force or load measured by the force measurement sensor 604 when the grip is in positions depicted in Frames (a) to (f).

In Frame (a) of 697, the grip is moving towards the specimen holder. Graph 696 depicts corresponding force reading at point (a) indicating that there is no load registered on the force sensor.

In Frame (b) of 697, the grip makes contact with the specimen holder. The lower wedge block's top surface is at the same level as that of the specimen holder plate's top surface. Graph 696 depicts corresponding force reading at point (b) indicating that there is no load registered on the force sensor. Just beyond the contact point, load registered by the force sensor starts to increase.

In Frame (c) of 697, the arm continues to push the grip forward. Since the forward motion of the wedge block 608 is stopped by the specimen holder plate 606, the wedge block 607 moves upward along the vertical slit boundary 613 and along slanted slit boundary 614, such that the gap between the wedge block faces increases. Graph 696 depicts the force readings along line from point (b) to point (c) indicating that the force registered on the force sensor increases linearly with forward displacement from the point the wedge block 608 touches the specimen holder plate 606. The point where the load registered by the force sensor starts to increase is registered as the contact point. The mechanism may be programmed to push the grip forward beyond this point by a specified amount, so that it opens up by a predetermined amount.

A specimen 616 is placed on the specimen holding plate 606, and extends onto the top surface of the gripper block 608.

In Frame (d) of 697, the arm starts to retract backwards closing the gap between the wedge faces. Graph 696 depicts corresponding force readings along curve (c) to (d) indicating decreasing load along the line (c) to (d). The backward force curve traces the forward force curve till the top gripper block 607 makes contact with the specimen. Thenceforth, it diverges.

In Frame (e) of 697, the arm continues to retract backwards closing the gap between the wedge faces even further to the point that the specimen gets gripped in between the wedge grip faces. Graph 696 depicts the corresponding force readings along curve (d) to (e).

In Frame (f) of 697, the arm has retracted away and lost physical contact with the specimen holder with the specimen gripped between wedge faces. The specimen is held by the wedge blocks and it pulls the grip forward. Graph 696 shows the corresponding force measurement at (f) with the opposite polarity compared to readings from (a) to (e). Once the gripper has lost contact with the specimen holder plate, the specimen holder plate may be retracted or lowered.

In an embodiment of the present invention, the load measurement polarity change is used as an indicator that the specimen has been completely gripped by the gripping mechanism, and the gripping mechanism is barely lifting off from the specimen holding plate 606. At or just beyond the polarity change, the specimen holder plate may be retracted or lowered.

Figure 6B:
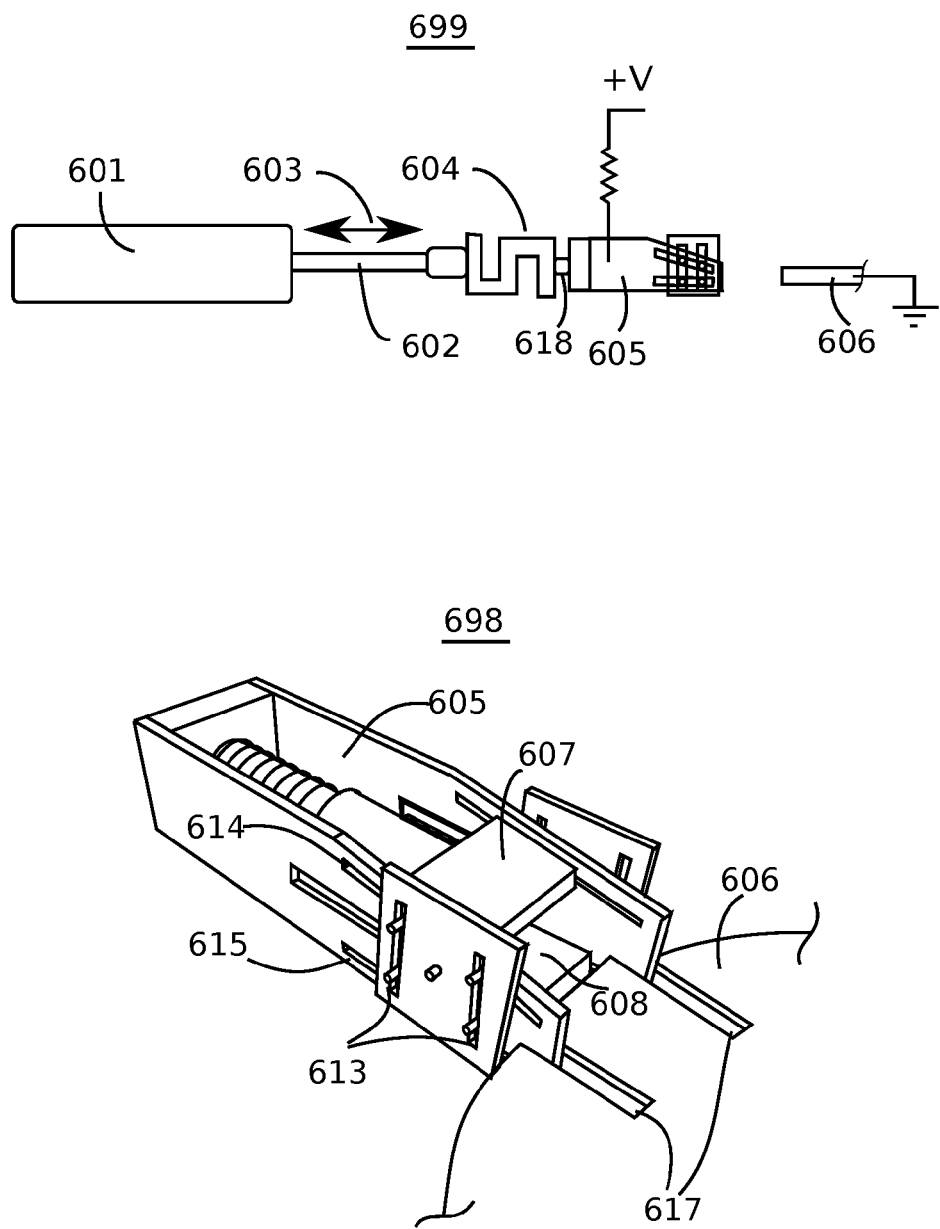
FIG. 6B illustrates an apparatus to load the specimen into a grip according to an embodiment of the present invention.

FIG. 6B illustrates an apparatus to load the specimen into a grip according to an embodiment of the present invention.

699 depicts a linear actuator arm comprising motor housing 601, retractable arm 602 that can move forward or backward along a straight line depicted by 603. 604 is a force measurement sensor such as a load cell. 604 is mechanically coupled to 602 by a coupler. 605 is a grip mechanism such as a wedge grip. 605 is mechanically coupled to 604 by a coupler 618. 606 is a specimen holding plate which can be used to place a specimen to be loaded into the grip assembly 605. In the position that they are not in contact with each other, gripper 605 and specimen holding plate 606 are electrically insulated from each other. A voltage supply +V is applied to 605 and a ground terminal is applied to 606 forming an electrical switch. 605 and 606 form two contacts of the switch. In an embodiment, gripper 605 is insulated from specimen holding plate 606 by using insulating material for all coupling elements of gripper 605 such as 618. The specimen loading plate boundary is such that the vertical grip faces can enter into the specimen holding area as shown in 698 through slits 617. The width of the slits 617 may be much larger than the entering plate thickness.

Figure 6C:
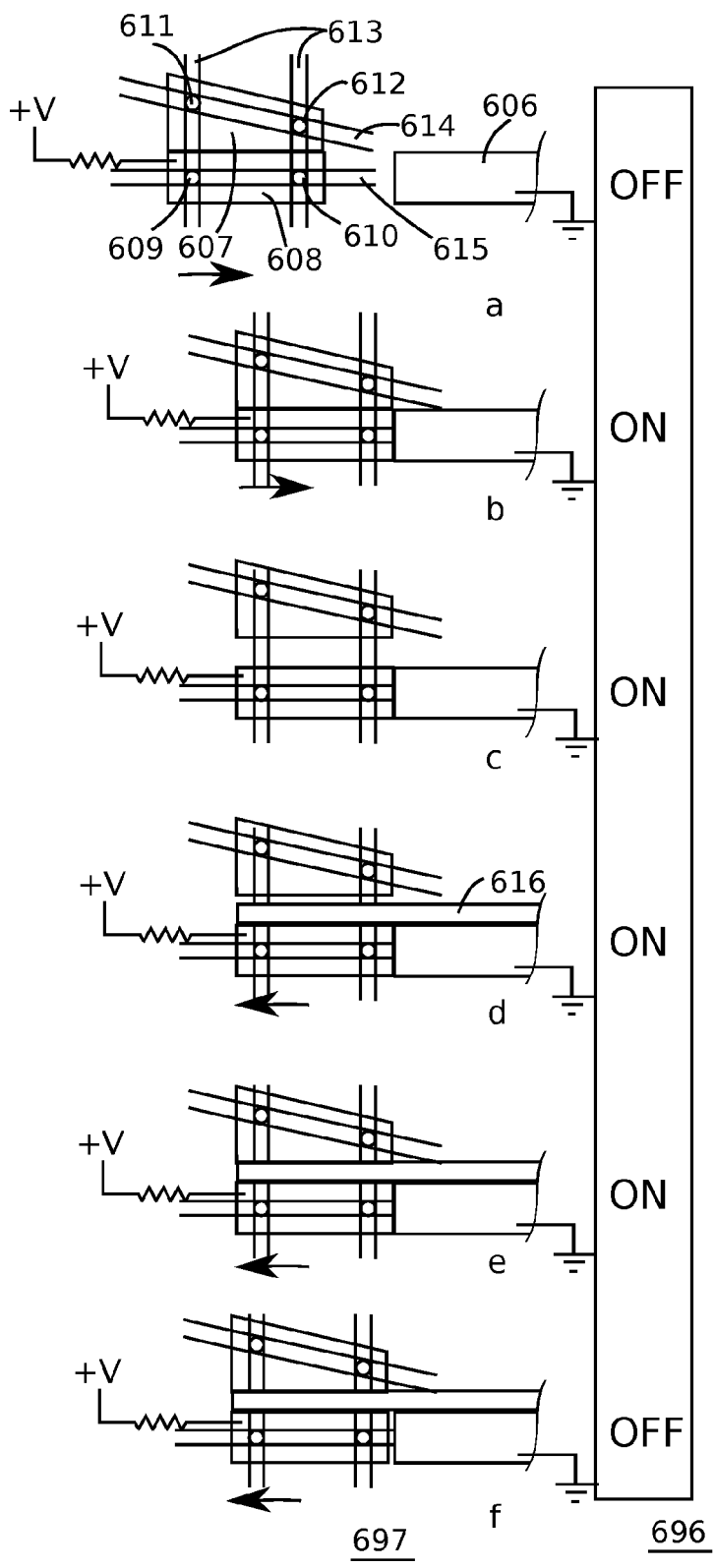
FIG. 6C illustrates steps in an exemplary method to load the specimen into a grip according to an embodiment of the present invention.

FIG. 6C illustrates steps in an exemplary method to load the specimen into a grip according to an embodiment of the present invention.

697 depicts a sequence of steps that occur in an exemplary method to load the specimen into the grip 605 where 605 is a wedge grip such as the one depicted in 698. 607 and 608 depict two wedge blocks in wedge grip 605 of 698. As shown in 697, the motion of the wedge block 607 is constrained by slits in external plates such that the wedge block pins 611 and 612 stay within the slanted slit boundary 614 and vertical slit boundary 613. Similarly, the motion of the wedge block 608 is constrained by external plates such that the wedge block pins 609 and 610 stay within the horizontal slit boundary 615 and vertical slit boundary 613. 606 depicts the specimen holding plate on which the specimen can be placed for loading into the grip.

Frames (a) to (f) in 697 depict the steps in specimen loading. 696 depicts the state of the switch formed by contacts 605 and 606 when the grip is in positions depicted in Frames (a) to (f).

In Frame (a) of 697, the grip is moving towards the specimen holder. 696 depicts corresponding switch state "OFF" at point (a) indicating that there is no contact between 605 and 606.

In Frame (b) of 697, the grip makes contact with the specimen holder. The lower wedge block surface is at the same level as that of the specimen holder plate. 696 depicts corresponding switch state "ON" at point (b).

In Frame (c) of 697, the arm continues to push the grip forward. Since the forward motion of the wedge block 608 is stopped by the specimen holder plate 606, the wedge block 607 moves upward along the vertical slit boundary 613 and along slanted slit boundary 614, such that the gap between the wedge block faces increases. 696 indicates that switch state remains "ON" from point (b) to point (c) indicating that 605 and 606 maintain contact. The point (depicted in (b)) where the state of the switch becomes "ON" is detected as the point of contact. The mechanism may be programmed to push the grip forward a specified amount beyond this point, so that it opens a predetermined amount.

In Frame (d) of 697, specimen 616 is loaded. The arm starts to retract backwards closing the gap between the wedge faces. 696 depicts corresponding switch state "ON" from positions (c) to (d) indicating 605 and 606 continue to remain in contact.

The specimen 616 is loaded onto the specimen holder plate, and extends onto the top surface of the bottom gripper.

In Frame (e) of 697, the arm continues to retract backwards closing the gap between the wedge faces even further to the point that the specimen gets gripped in between the wedge grip faces. 696 depicts switch state "ON" at positions (d) to (e).

In Frame (f) of 697, the arm has retracted away and lost physical contact with the specimen holder with the specimen gripped between wedge faces. The specimen is held by the wedge blocks and it pulls the grip forward. 696 shows the corresponding switch state "OFF" at (f) which is indicative of the specimen being loaded. The further stretching of the specimen may be done assuming the point of loss of contact as the baseline. For example, for achieving uniform stretching of a particular amount, each gripper will be moved away by that specified distance from it's corresponding loss-of-contact point.

Figure 7:
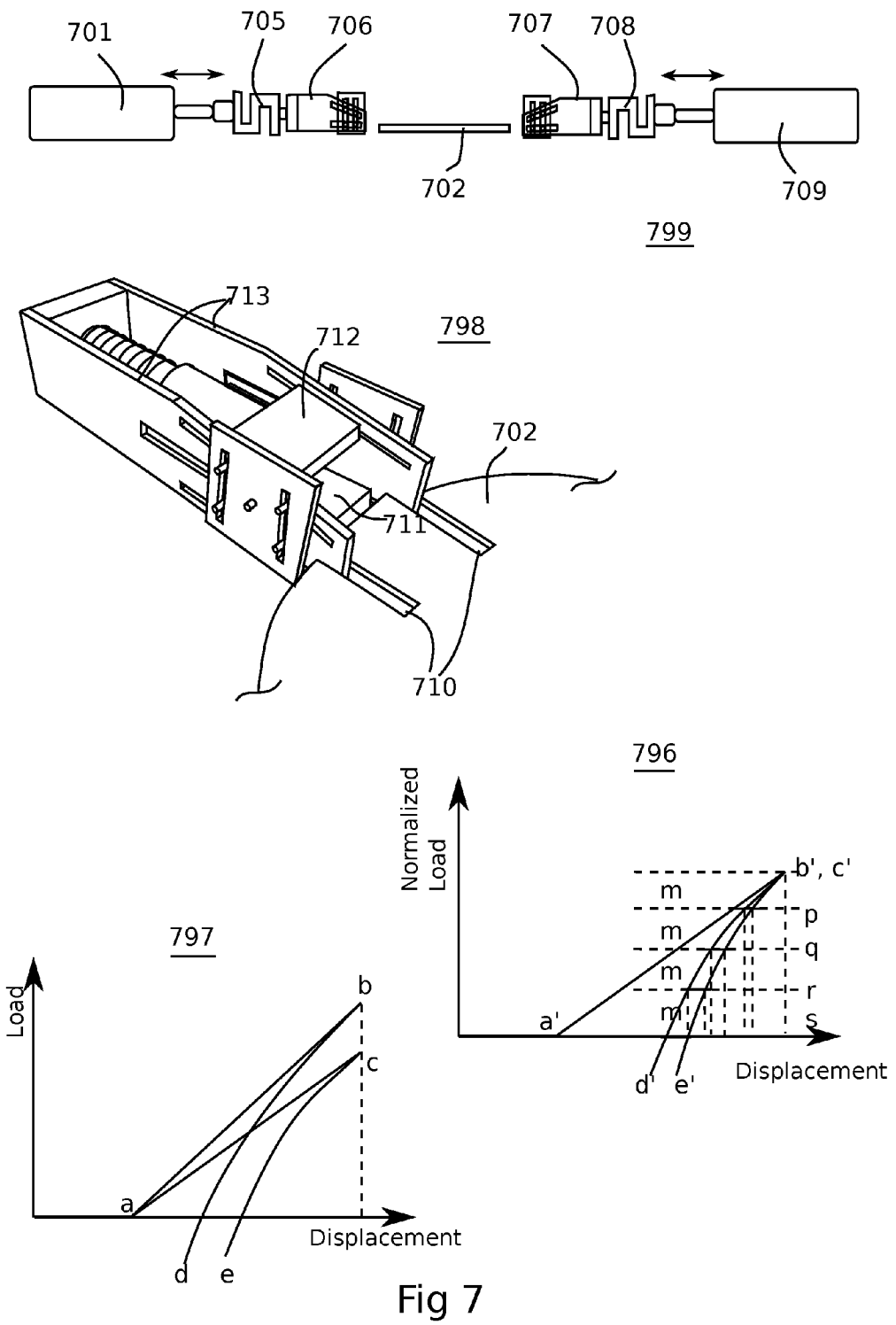
FIG. 7 illustrates a method for simultaneously loading the specimen in two or more grips by controlling the motion of the grips.

FIG. 7 illustrates a method for simultaneously loading the specimen in two or more grips by controlling the motion of the grips.

799 illustrates an exemplary setup comprising two linear actuator arms, but more than two arms may be involved in this method. 701 is a linear actuator mechanically coupled to force measurement sensor 705 which is mechanically coupled to grip 706. 709 is another linear actuator mechanically coupled to force measurement sensor 708 which is mechanically coupled to grip 707. 702 depicts specimen holder plate with slits 710 as shown in 798. The gap between the wedges 711 and 712 in 798 increases as the block 711 is obstructed by the specimen holder plate when the grip moves such that plates 713 enter the specimen plate slits 710. Specimen is loaded between the gap in wedge blocks 712 and 711. After specimen placement, the two grips 706 and 707 in 799 are pulled away from the specimen holder 702. As the grip moves away from the specimen holder, the gap between the wedge blocks begins to close and the specimen is gripped by the wedge block faces.

An exemplary control scheme to ensure that both grips hold the specimen at the same time is described below.

Graphs 797 and 796 depict load vs displacement graphs. Load is the force measured on the force measurement sensor. Displacement is the distance that a grip travels from its start position towards the specimen holder. In other words, greater the displacement of the grip, the closer it is to the specimen holder.

Graph 797 depicts load measured by force measurement sensors at various grip displacement positions. Curve (a)(b) depicts force measurements on force measurement sensors 705 as the grip 706 travels connects and travels into the specimen holder plate 702, while opening up. The specimen is placed in the grip 706 after it attains displacement at (b). As the gripper starts to close, the closing curve traces the opening curve for some distance (till the gripper starts gripping the specimen) at which time it diverges. Curve (b)(d) depicts force measurement on force measurement sensor 705 as the grip 706 retracts and travels away from the specimen holder plate 702. Curve (a)(c) depicts force measurements on force measurement sensors 708 as the grip 707 travels connects and travels into the specimen holder plate 702, while opening up. The specimen is placed in the grip 707 after it attains displacement at (c). Curve (c)(e) depicts force measurement on force measurement sensor 708 as the grip 707 retracts and travels away from the specimen holder plate 702.

The slopes of the lines (a)(b) and (a)(c) may different. This may happen due to setup variations such as difference in spring stiffness inside the grip. Curves (b)(d) and (c)(e) have different characteristics which is expected due to difference in specimen thickness and characteristics as well as differences in the grips.

Graph 796 depicts normalized load graphs. The curve (a)(b) (d) in 797 is divided by the slope of line segment (a) (b) to get curve (a')(b')(d') in 796. Similarly, the curve (a)(c)(e) in 797 is divided by the slope of line segment (a)(c) to get curve (a')(c')(e') in 796. This causes (b') and (c') to coincide, since the total displacement from (a) to (b) and (a) to (c) (and hence from (a') to (b') and from (a') to (c')) is the same. This is ensured by controlling the grips to travel the same amount beyond the contact point (a).

796 also depicts a control scheme used to move the actuator arms after specimen has been placed on the grip faces such that both the grips hold the specimen at the same time. The control scheme moves the actuator arms to achieve a displacement such that the normalized load on the arms is decreased by the same amount depicted by (m) at each step. (p), (q), (r) and (s) depict normalized load levels at intervals (m) from the starting displacement (b'). (s) depicts zero normalized load which indicates that the grip has held the specimen and is just about to leave the specimen holder plate. The control algorithm works such that the normalized loads (p), (q) and so forth are achieved simultaneously or as simultaneously as possible on all the involved grips.

If the normalized load step (m) is chosen small enough, both the grips would hold the specimen almost simultaneously after the last displacement step. In other words, the difference in the time instants when the grips hold their respective specimen ends can be made smaller by choosing a smaller normalized load step (m).

The method may also be applied for more than two grips by adjusting displacements of the multiple grips one after the other in a circular order, or all at the same time, such that all grips are adjusted to the same normalized load before the first grip is moved again. Using this control scheme, more than one grips can hold the specimen simultaneously.

Figure 8A:
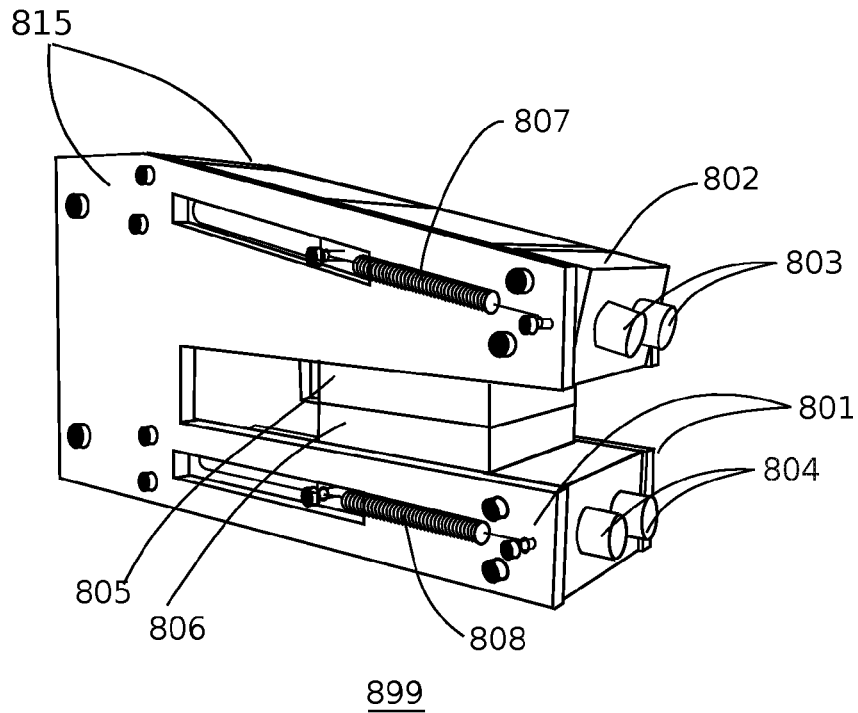
FIGS. 8A and 8B illustrate an exemplary gripping mechanism according to one embodiment of the present invention.
Figure 8A:
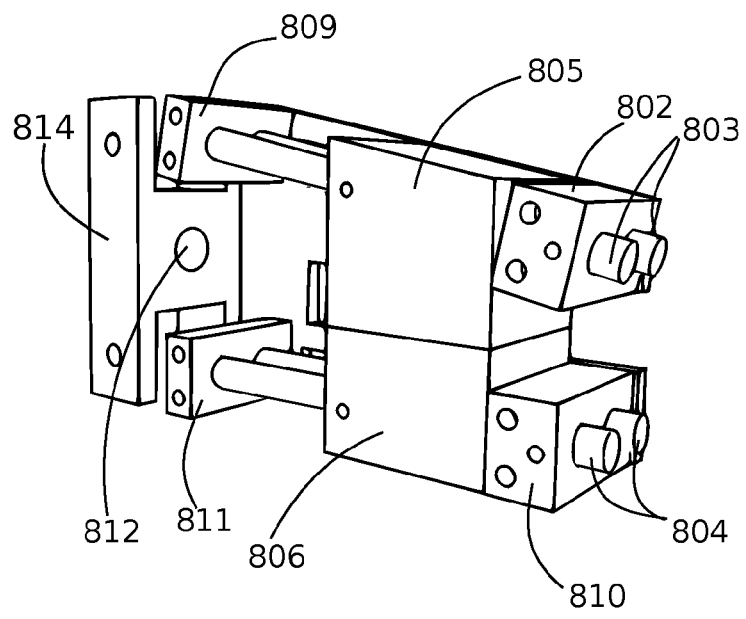
Figure 8B:
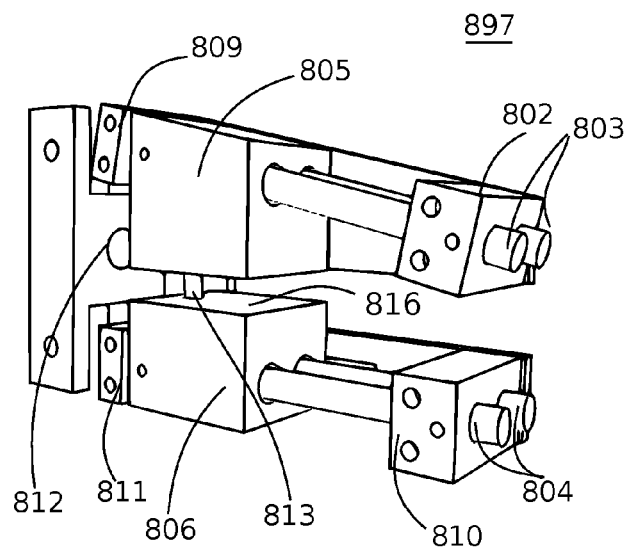

FIGS. 8A and 8B illustrate an exemplary gripping mechanism 899 according to one embodiment of the present invention.

The gripping mechanism comprises a base block 814 on which two side plates 815 are mounted. Surface 816 acts as the gripping surface between two blocks 805 and 806. The motion of blocks 805 and 806 is constrained by guide rails 803 and 804. Guide rail 804 is in the horizontal direction whereas guide rail 803 makes an angle with the horizontal direction. A connecting guide rail or rod 813 constrains the blocks to move together along the horizontal direction. The connecting rod 813 is inserted in matching bores on the gripping surfaces of the gripping blocks. Since guide rails 803 are at an angle with respect to the horizontal direction, guide block 805 moves vertically as it moves along the horizontal direction. Springs 807 and 808 (and similar springs on the other side) pull guide blocks 805 and 806 such that block 805 moves horizontally as well as vertically downwards and meets block 806 at the surface 816 of block 806.

898 depicts internal components of exemplary gripping mechanism when the grip is closed. For loading a specimen to be gripped into the gripping surface, the block 806 may be forced to move away from the springs such that the springs get more and more extended and pull more strongly on the blocks. Since 806 and 805 are mechanically constrained to move together by guide rail 813, the gap above surface 816 increases. The grip is said to be open in this configuration. 897 depicts internal components of exemplary gripping mechanism when the grip is in this open configuration.

For gripping the specimen in between blocks 805 and 806, the force that was used to move block 806 away from the springs is released causing the springs to pull the blocks back to their original state. While the blocks move towards the springs, the gap above the surface 816 reduces thus clamping the specimen which is placed in this gap.

A force acting on the specimen tries to pull the specimen out of the gripping surface. However, due to friction between the specimen and gripping surfaces, the blocks 805 and 806 are pulled such that the gap above the gripping surface 816 is reduced, further tightening the grip. In this manner, the grip has a self tightening action.

In one embodiment, very low friction exists between guide rails 803, 804 and guide blocks 805, 806. Low friction may be achieved by coating the inner surface of the bore in contact with the guide rails with teflon or other low-friction surface coating. In one embodiment, bearings are used to reduce friction.

In one embodiment, the gripping surface has serrations which increase the friction between the gripping surface and the specimen.

Figure 9A:
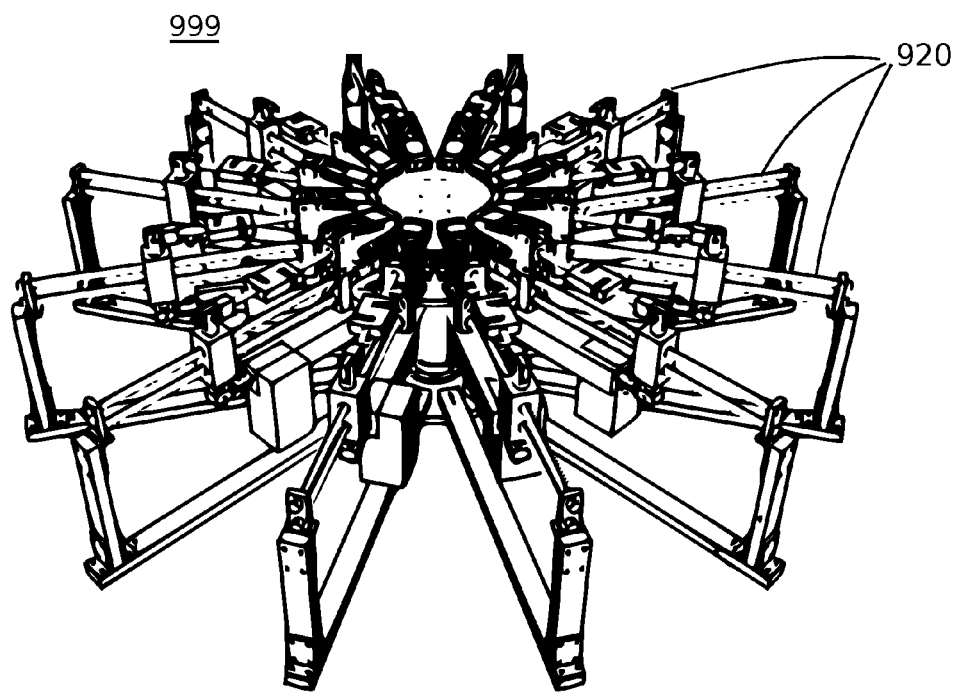
FIGS. 9A and 9B illustrate a materials testing machine according to one embodiment of the present invention.
Figure 9B:
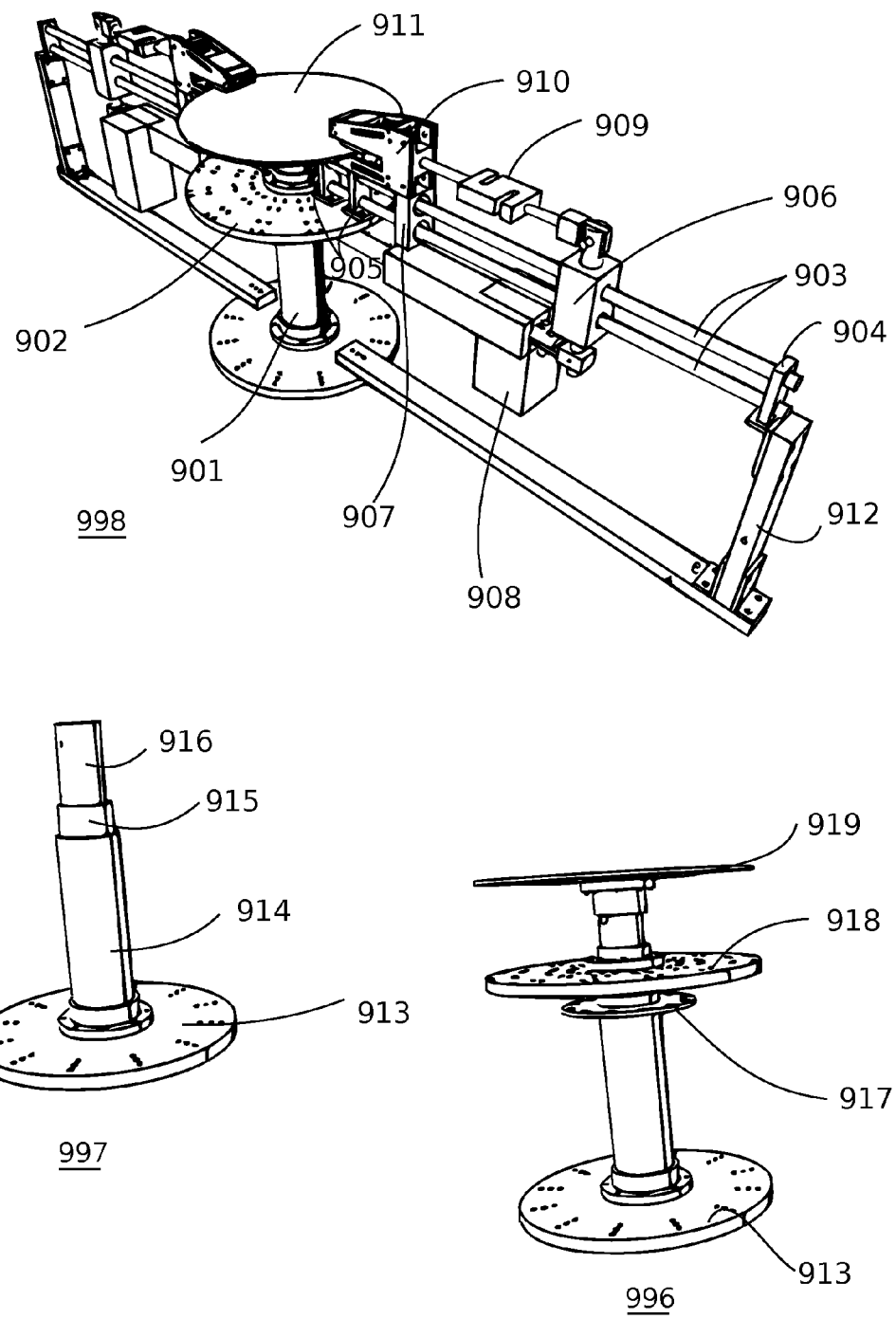

FIGS. 9A and 9B illustrate a materials testing machine according to one embodiment of the present invention. 999 depicts a materials testing machine comprising multiple arms 920. In one embodiment, the materials testing machine has 12 arms. 998 depicts the same exemplary materials testing machine with only two arms shown (the other arms are not drawn, but they exist).

Each arm comprises a wedge grip 910, a load cell 909 and a linear actuator 908. Specimen in the form of circular sheet is placed in the jaws of the wedge grips. Once the specimen is loaded, the linear actuators pull the specimen radially outward. In one embodiment, the arms pull the specimen radially out such that each actuator pulls with the same force. A camera based extensometer, not shown in figure, monitors specimen stretch from above the specimen. A computer system acquires data from the load cells, the camera system, and optional linear displacement sensors and records the data.

In one embodiment of the present invention, the extensometer is included in the actuator 908 itself, by way of linear displacement sensors in each actuator.

997 depicts details of the construction of the materials testing machine depicted in 999. 997 depicts the central column assembly of exemplary materials testing machine. The column assembly comprises a base plate 913. Cylindrical columns 914, 915 and 916 are inserted one inside another. The circumference of each cylindrical column provides a level on which a flange is mounted. 996 depicts central column assembly and level plates' assembly of the exemplary material testing machine. 917 depicts a flange which is mounted on cylindrical column 914. 918 depicts a flange which is mounted on column 915. 919 depicts a flange which is mounted on 916.

Flange 917 has precision holes on which one end of the actuator is mounted. The other end of the actuator rests on the guide block 906. In an embodiment, the linear actuator has an extending arm and a motor. The motor end of the linear actuator is near the guide block 906, so as to make the machine more compact. Flange 918 has precision drilled holes on which end supports of the guide rods 903 are mounted. Flange 919 provides a level surface for specimen loading. During loading the level of flange 919 is raised such that it is at the same level as the wedge grip jaw surface on which the specimen is to be gripped. After specimen loading the flange 919 is lowered so that it does not interfere with measurement process.

Figure 10:
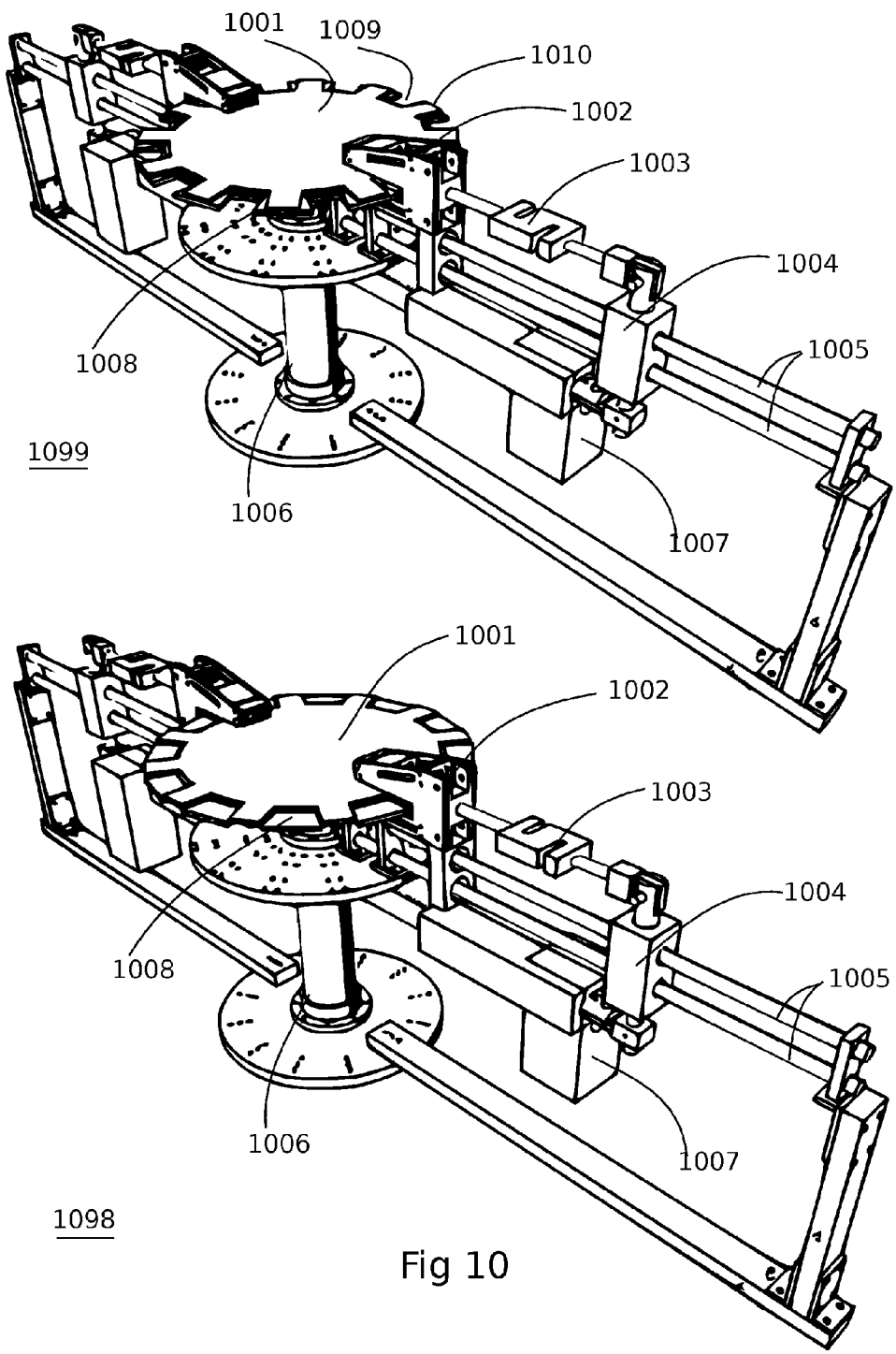
FIG. 10 illustrates a method for automatic loading of specimen in two or more grips according to one embodiment of the present invention.

FIG. 10 illustrates a method for automatic loading of specimen in two or more grips according to one embodiment of the present invention. In one embodiment, the specimen loading is automatic and the two or more grips grip the specimen simultaneously.

The mechanism comprises a specimen loading plate 1008 on which specimen 1001 rests. The specimen loading plate is composed of a central rotating disc and a fixed peripheral plate. The central rotating disc has raised tabs. The entire assembly can be raised or lowered. During specimen loading the plate 1008 is raised such that the specimen surface is at the same level as the gripping jaw of the wedge grip.

1099 depicts the specimen loading mechanism in loading position in an embodiment of the present invention. The specimen tabs (extensions beyond the circular region of the specimen) rest on the fixed peripheral plate such that they align with the tabs on the fixed peripheral plate 1010. The fixed peripheral plate has rectangular regions 1009 (rectangular indentations) where the wedge grips can dock. The wedge grip docks and the gap between wedge faces increases as the wedge grip moves towards the specimen to facilitate specimen loading. Once the gap between wedge faces has increased to its maximum value or to a preset value, the central rotating disc rotates such that the specimen 1001 rotates and the specimen tabs lie in the gripping area of the wedge grip. In one embodiment, the central rotating disc is rotated using a motor automatically. 1098 depicts the specimen in this rotated position, ready for gripping by the wedge grip.

The wedge grip is coupled to the actuator 1007 arm via load cell 1003 and guide block 1004. The actuator 1007 moves the wedge along the guide rails. To grip the specimen, the actuator moves the wedge grip away from the specimen. This causes the grip to close and clamp the specimen in its jaws. In one embodiment, the specimen is gripped simultaneously by controlling the motion of the actuators according to feedback from the load cell sensors. In another embodiment, opening and gripping positions are controlled relative to the position where each gripper meets the fixed peripheral plate. This position may be detected by the electrically detecting the contact between the gripper and the fixed peripheral plate, by using them both as electrodes, as described above.

Once the specimen is gripped, the plate 1008 is lowered such that it does not interfere with the measurement process. In one embodiment, the plate 1008 is lowered automatically using a motor or linear actuator.

Figure 11:
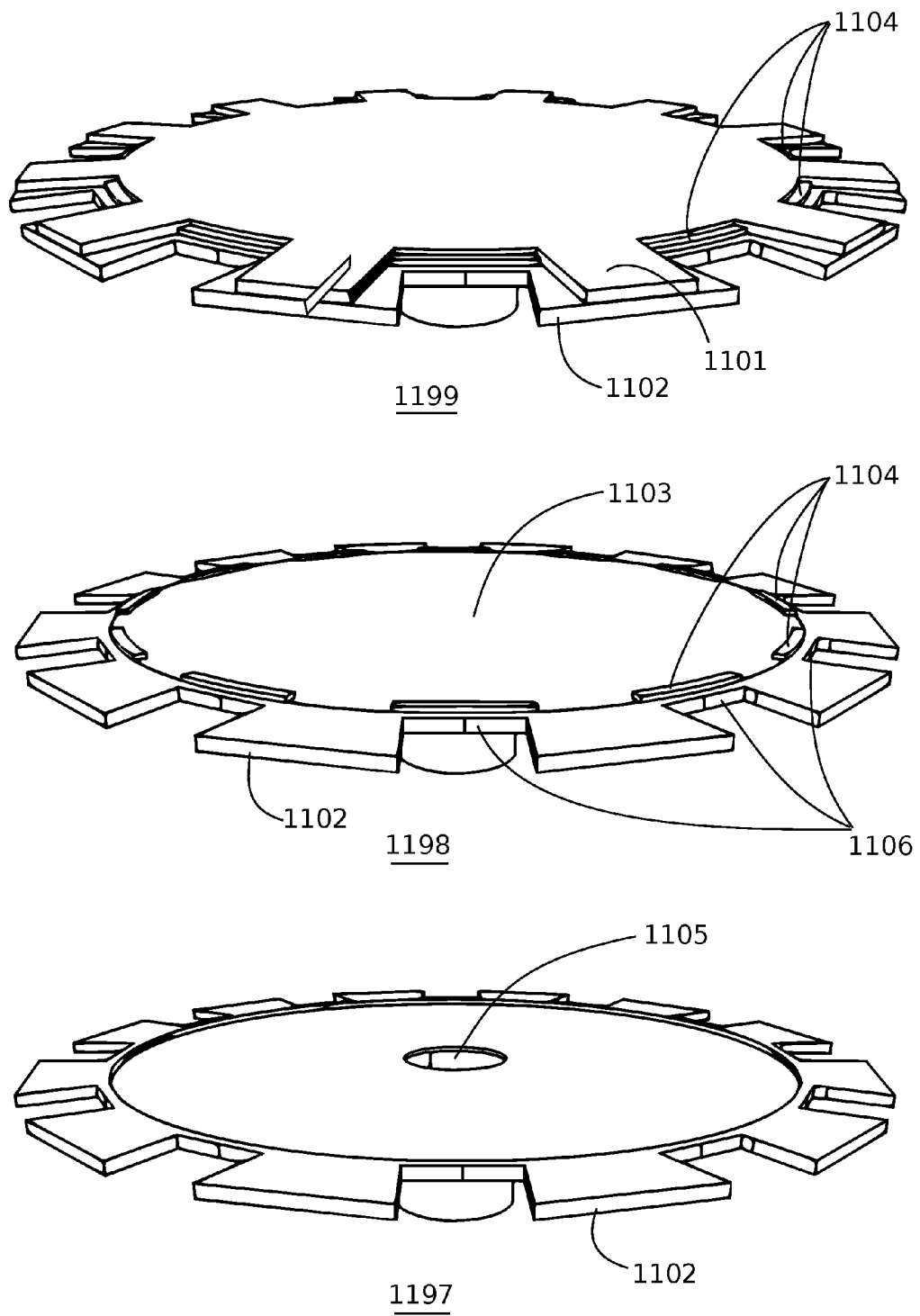
FIG. 11 illustrates sub parts of the specimen loading mechanism according to an embodiment of the present invention.

FIG. 11 illustrates sub parts of the specimen loading mechanism according to an embodiment of the present invention.

1199 depicts sub parts of the specimen loading mechanism. 1101 depicts the specimen sheet which is cut into a shape which is circular with rectangular sections for gripping. The specimen loading mechanism has a central rotating disc 1103 and a fixed peripheral plate 1102. The central rotating plate 1103 has raised tabs 1104 for precise specimen placement. The central rotating disc 1103 is rotated such that the rectangular regions of the specimen are placed into the wedge grip gripping area. The fixed peripheral plate 1102 has rectangular regions 1106 (rectangular indentations) at which the wedge grips of the materials testing machine as depicted in 999 can dock. The fixed peripheral plate has central bore 1105 such that it can be fit onto the central column assembly of the materials testing machine such as one depicted in FIG. 9.

In one embodiment, the central rotating disc is coupled to a motor system which can rotate the disc by desired amount. In one embodiment, the motor assembly is located in the bore 1105 of the fixed peripheral plate.

In one embodiment, the central bore 1105 has a rack and pinion arrangement to raise or lower the specimen loading mechanism. In one embodiment, the specimen loading mechanism is raised and lowered using a motor assembly.

In one embodiment, the wedge grip jaw face on which the specimen is to rest has a fillet radius along the edge over which the specimen slides into the jaw face. This is done to prevent the specimen edge to fold or interfere in any manner with the jaw face due to slight level mismatch while rotating the specimen.

Figure 12:
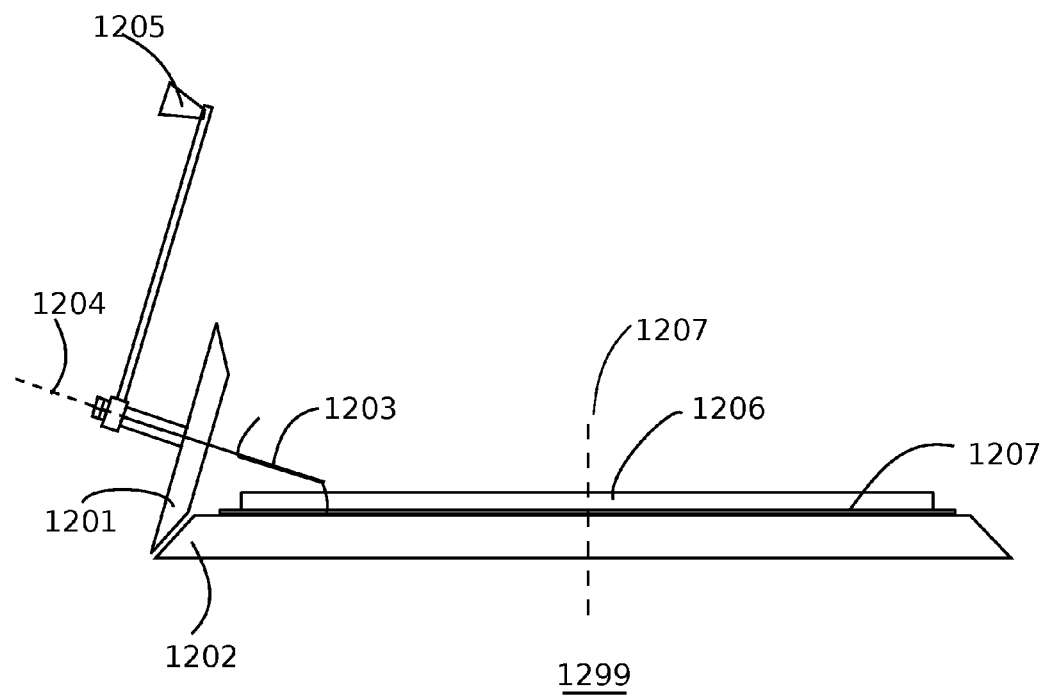
FIG. 12 illustrates front view of a tool for cutting out specimen shape from a sheet of specimen in an embodiment of the present invention.

FIG. 12 illustrates front view of a tool for cutting out specimen shape from a sheet of specimen in an embodiment of the present invention.

1299 depicts an exemplary cutting tool which can cut a circular sheet of specimen with rectangular regions for specimen gripping. The cutting tool 1299 comprises a rotating base 1202, soft specimen holding base 1207, a rotating cutter 1203 mounted on a rotating base 1201 which is rotated using a handle 1205. 1206 depicts the specimen sample to be cut into a particular shape.

Base 1202 is capable of rotating along axis 1207 and is coupled to rotating base 1201 using gears which have a specific gearing ratio. In one embodiment, the gears are bevel gears. The gearing ratio between 1201 and 1202 is predetermined based on the shape of the cut specimen desired. The gearing ratio is the same as the symmetry number of the specimen shape to be cut. In other words, the gearing ratio is the same as the number of actuator arms of the material testing machine. The rotating base 1201 rotates around axis of rotation 1204 which makes a certain angle with the horizontal base. Rotating base 1201 has a cutter 1203 mounted along the axis of rotation 1204. The angle between axis 1204 and horizontal is predetermined based on the shape of the cut specimen desired. In one embodiment, the angle of the axis 1204 to the horizontal is a function of the diameter of the circle along which the cutter edge moves and the radius of the specimen. In one embodiment the angle between the axis 1204 and horizontal is arcsin(1/N) where N is the number of symmetric sections to be cut in the specimen. The shape of the cutter 1203 is predetermined based on the shape of the specimen desired. Handle 1205 facilitates user to rotate the rotating base 1201 and thereby cut the specimen.

In one embodiment, the rotating base 1201 is rotated using a motor for automatic specimen cutting.

In one embodiment, the soft specimen base 1207 is not placed under the specimen.

In one embodiment, the gearing ratio between 1202 and 1201 is obtained using a gear train enabling use of smaller gears facilitating easier manufacturing. In one embodiment, a small circular gear is mounted with its axis along 1207 and teeth in the horizontal plane. A gear train comprising two vertical circular gears at ends of an axle is used. One gear couples to the said gear with its axis along 1207 while the other gear is at the far end of the axle and couples to gear teeth on 1201.

Figure 13:
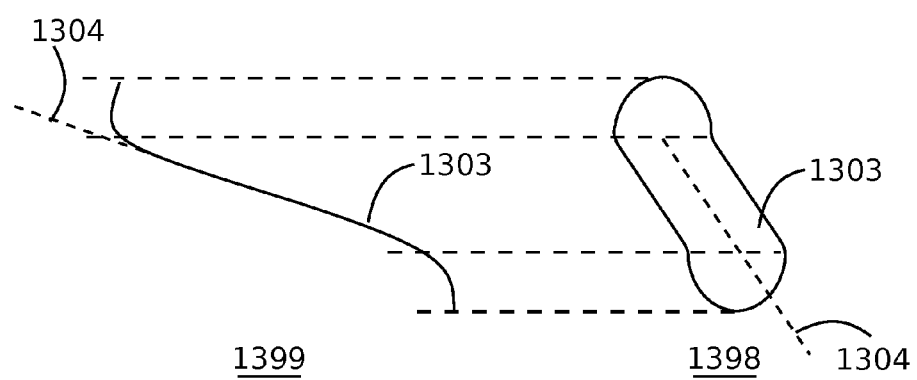
FIG. 13 illustrates the cutting blade of a tool for cutting the specimen shape, according to an embodiment.

FIG. 13 illustrates the cutting blade of a tool for cutting the specimen shape, according to an embodiment. 1399 depicts the side view of a cutting blade 1303. The blade 1303 rotates around axis 1304. 1398 depicts the three-quarter view of the same cutting blade 1303. The cutting blade is made out of a circular section, a rectangular section and another circular section. The upper circular section cuts the outer circle (extremities of the tabs), while the lower circular section cuts the inner circle of the material sample sheet. The two edges of the rectangular part cut the sides of the tab extensions of the sample. In an embodiment, this cutting blade is made starting from a planar piece of appropriate shape and bending it in two places, namely at the folds between the rectangular and circular sections.

A universal materials testing machine is disclosed. It is understood that the embodiments described herein are for the purpose of elucidation and should not be considered limiting the subject matter of the present patent. Various modifications, uses, substitutions, recombinations, improvements, methods of productions without departing from the scope or spirit of the present invention would be evident to a person skilled in the art.

The invention claimed is:

1. An apparatus comprising:
   a plurality of linear actuators,
   load cells attached to each of the linear actuators,
   grippers attached to each of the load cells,
   a first plate, and
   a data collection system, wherein
   the grippers can simultaneously grip a material sample and pull it outwards,
   the grippers each have two gripping blocks configured to move on guides in such a way that as they move on the guides towards their respective linear actuator, the distance between the gripping blocks increases,
   the first plate is configured to contact one of the gripping blocks of each of the grippers at geometric contact points and configured in such a way that the grippers may be pushed beyond the respective geometric contact points with the first plate, causing the grippers to open, and
   the data collection system collects force data from the load cells and geometric data.

2. The apparatus of claim 1 wherein the geometric data is collected from linear displacement sensors.

3. The apparatus of claim 1 wherein the geometric data is collected from a camera capturing an image of the material sample.

4. The apparatus of claim 3 wherein the material sample has a specific pattern imprinted on it and an image processing means tracks points and/or shapes in the pattern to generate geometric data.

* * * * *